US006197558B1

(12) United States Patent
Fotheringham

(10) Patent No.: US 6,197,558 B1
(45) Date of Patent: *Mar. 6, 2001

(54) TRANSAMINASE BIOTRANSFORMATION PROCESS

(75) Inventor: Ian G. Fotheringham, Vernon Hills, IL (US)

(73) Assignee: NSC Technologies, Mt. Prospect, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/858,111

(22) Filed: May 19, 1997

(51) Int. Cl.[7] .............................. C12P 13/04; C12N 1/12; C12N 15/00; C12N 1/00
(52) U.S. Cl. ................... 435/106; 435/252.1; 435/320.1; 435/243; 435/193
(58) Field of Search ................... 435/106, 69.1, 435/252.1, 320.1, 243, 193

(56) References Cited

U.S. PATENT DOCUMENTS

| | | | |
|---|---|---|---|
| 4,518,692 | 5/1985 | Rozzell | 435/116 |
| 4,826,766 | 5/1989 | Rozzell | 435/106 |
| 4,880,738 | 11/1989 | Rozzell | 435/106 |
| 5,316,943 * | 5/1994 | Kidman et al. | 435/280 |
| 5,420,021 * | 5/1995 | Marugg et al. | 435/74 |

FOREIGN PATENT DOCUMENTS

500188 A2   8/1992   (EP).

OTHER PUBLICATIONS

A. Aristidou, Biotechnol Prog., 1995, vol. 11, pp. 475–478.
C. Platteeuw, Applied and Environmental Microbiology, 1995, vol. 61, pp. 3967–3971.
J. Marugg, Applied and Environmental Microbiology, 1994, vol. 60, pp. 1390–1394.
I. Fotheringham, BioChem J., 1986, vol. 234, pp. 593–604.

* cited by examiner

Primary Examiner—Ponnathapu Achutamurthy
Assistant Examiner—Peter Tung
(74) Attorney, Agent, or Firm—Fitzpatrick, Cella, Harper & Scinto

(57) ABSTRACT

A process for making natural and unnatural amino acids which comprises reacting a first amino acid, a keto acid and a transaminase enzyme under conditions appropriate to produce a second amino acid and pyruvate; reacting the pyruvate with acetolactate synthase under conditions appropriate to produce a compound that does not react with the transaminase enzyme and separating the second amino acid.

79 Claims, 13 Drawing Sheets

TRANSAMINASE BIOTRANSFORMATION PROCESS

BACKGROUND OF THE INVENTION

1. Field of the Invention

This invention relates to a process for producing amino acids employing aminotransferases. More particularly, this invention relates to a process for making unnatural amino acids such as L-2-aminobutyrate and L-tert-leucine employing an aminotransferase.

2. Related Background Art

The process of the invention improves on prior art processes for making natural and unnatural amino acids using transaminase enzymes. Transaminases have been known in the literature for many years. See, Transaminases, Philipp Christen & David E. Metzler, ed. (1985) (John Wiley and Sons, New York). Briefly, a transaminase reaction requires two substrates, an amino acid and a keto acid. The transaminase catalyzes the exchange of the keto group (C=) from the keto acid and the amino group from the amino acid (—$NH_2$). This exchange generates a new amino acid from the keto acid and a new keto acid from the amino acid. Typically only one of the products is desired, generally the new amino acid, and the other is an unwanted by-product.

Used in isolation, the enzyme converts the two substrates to the two products. Theoretically, because the reaction is reversible, it proceeds until it reaches equilibrium producing roughly 50% conversion of the substrate to products.

U.S. Pat. No. 4,518,692 ("Rozzell I") discloses a method for producing L-amino acids by reacting L-aspartic acid and various 2-keto acids with transaminases. The Rozzell I method uses L-aspartic acid as the amino acid to produce oxaloacetate and describes various methods of decarboxylating oxaloacetate to form pyruvate. However, as will be shown herein, the pyruvate produced in the Rozzell I method can still act as a keto donor in the reverse process to form alanine. Tokarski et al., *Biotechnology Letters*, Vol. 10 (1) (1988), pp. 7–10, show that alanine acts as a substrate in transaminase reactions. See also, *Transaminases* (1985); and *Amino Acids: Biosynthesis and Genetic Regulation*, Klaus M. Herrmann and Ronald L. Somerville ed. (1983) (Addison-Wesley Publishing, Reading Mass.). Tokarski, et al. studied the use of a transaminase to produce L-2-aminobutyrate from 2-ketobutyrate and alanine. The reference, however, discloses only 25–30% conversion to products, demonstrating that the reverse reaction will prevent attaining even the theoretical limit of 50%. This has long been considered an intrinsic property and a problem of transaminase reactions and is the major reason such enzyme catalyzed reactions have not been exploited more in industrial processes to produce these highly desired amino acid products. The present invention differs from Rozzell I and Tokarski et al. by providing an effective enzymatic method to remove the potential substrates of the reverse reaction from the mixture.

U.S. Pat. No. 4,826,766 ("Rozzell II"), discloses an improved transaminase catalyzed reaction that employs two transaminase enzymes and additional keto acids. In the process, a first transaminase enzyme catalyzes the reaction between a first amino acid and a first keto acid to produce a second amino acid and second keto acid. A second transaminase enzyme then catalyzes a further reaction of the second amino acid and a third keto acid to form the desired amino acid. The two transaminase enzymes are selected such that the first enzyme does not catalyze the second reaction and the second enzyme does not catalyze the first reaction. The Rozzell II method, however, requires additional keto acid and does not disclose the use of acetolactate synthase.

The disclosure of these patents and references are hereby incorporated in their entirety into this specification by reference. Thus, a method to increase the yield of amino acids using transaminase enzymes is desirable.

This invention provides an improved transaminase process, which combines the transaminase enzyme with a second enzyme that eliminates the keto acid produced by the transaminase reaction, preventing the formation of equilibrium, and driving the amino acid producing reaction to completion. The second enzyme catalyzes a reaction which converts the keto acid to a substance that can no longer react with the transaminase. By removing the second keto acid, the second enzyme allows the amino acid producing reaction to proceed to an extent that the desired amino acid product represents approximately 100% of the amino acids produced.

The amino acids produced by this process are useful by themselves, for example as feed additives, flavor enhancers, sweeteners, and nutritional supplements, or can be used as synthetic intermediates to be further reacted to form useful products, in particular pharmaceuticals. Amino acid products of this process are particularly useful as single enantiomer starting materials for producing chiral pharmaceuticals.

SUMMARY OF THE INVENTION

This invention provides a process for making an amino acid which comprises reacting a first amino acid, a first keto acid and a transaminase enzyme under conditions appropriate to produce a second amino acid and pyruvate; and reacting the pyruvate with acetolactate synthase under conditions appropriate to produce a compound that does not react with the transaminase enzyme.

The invention also provides a process for producing an amino acid which comprises:

a) reacting a first amino acid with an enzyme under conditions appropriate to produce a keto acid;

b) reacting the keto acid with a second amino acid and a transaminase enzyme under conditions appropriate to produce a third amino acid and pyruvate; and c) reacting pyruvate with acetolactate synthase.

The invention further provides a process for making L-2-aminobutyrate comprising:

a) reacting L-threonine with threonine deaminase under conditions appropriate to produce 2-ketobutyrate;

b) reacting the 2-ketobutyrate, L-aspartate and transaminase enzyme under conditions appropriate to produce oxolactate and L-2-aminobutyrate;

c) allowing the oxolactate to form pyruvate;

d) reacting the pyruvate with acetolactate synthase enzyme under conditions appropriate to produce acetolactate;

e) allowing the acetolactate to form acetoin; and f) separately recovering acetoin and L-2-aminobutyrate.

The invention also provides a process for producing 2-amino butyrate which comprises:

a) reacting L-threonine with a threonine deaminase enzyme under conditions appropriate to produce 2-ketobutyrate;

b) reacting 2-ketobutyrate with an amino acid and transaminase enzyme under conditions appropriate to produce 2-aminobutyrate and pyruvate; and c) reacting pyruvate with acetolactate synthase enzyme under conditions appropriate to produce a compound that does not react with transaminase enzyme.

The invention also provides a reaction medium comprising a keto acid, an amino acid, transaminase enzyme, and acetolactate synthase enzyme.

DETAILED DESCRIPTION OF THE INVENTION

Figure 1:
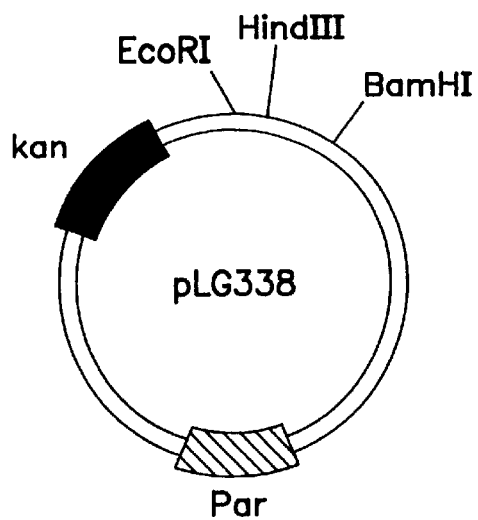
FIG. 1 shows the production of plasmid pIF349 from plasmid pLG338 discussed in Example 6 below.
Figure 1:
Figure 1:
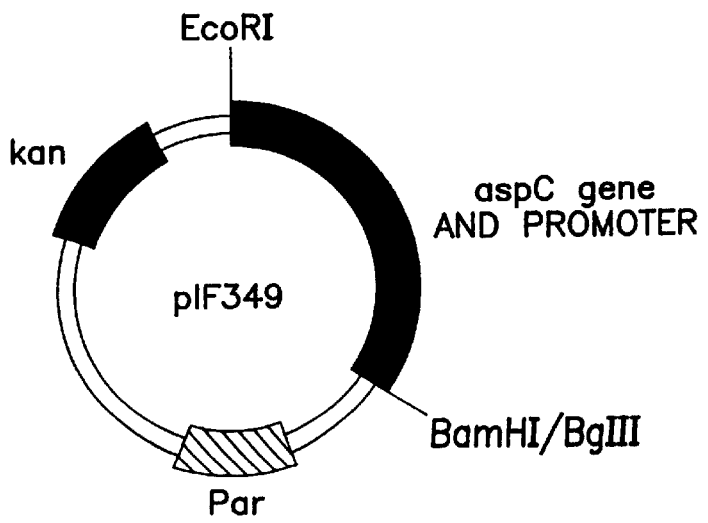
Figure 2:
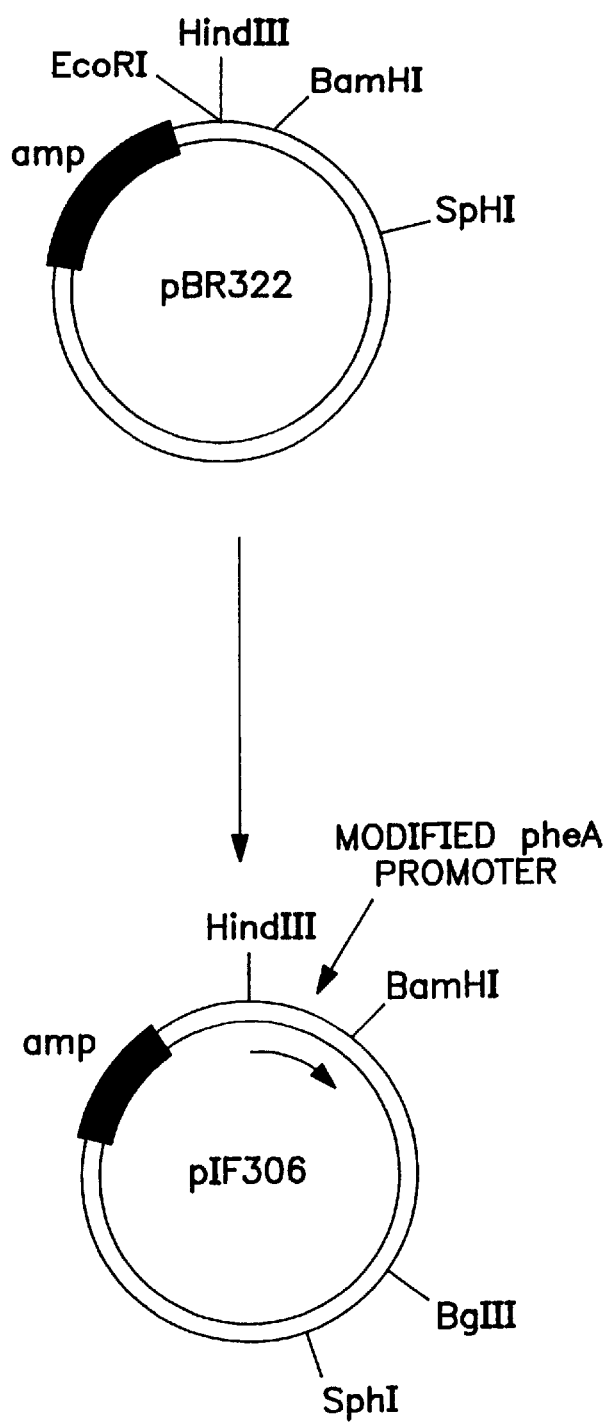
FIG. 2 shows the production of plasmid pIF306 from plasmid pBR322 discussed in Example 1 below.
Figure 3:
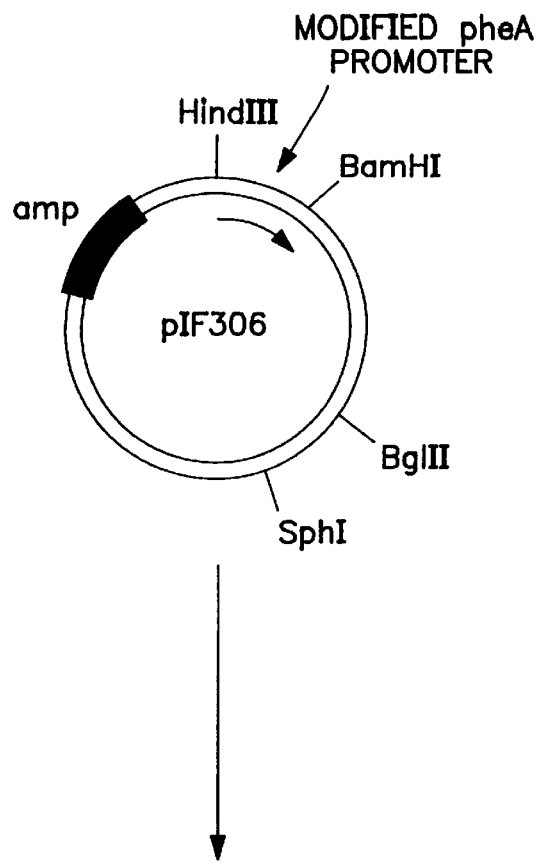
FIG. 3 shows the production of plasmid pIF307 from plasmid pIF306 discussed in Example 1 below.
Figure 3:
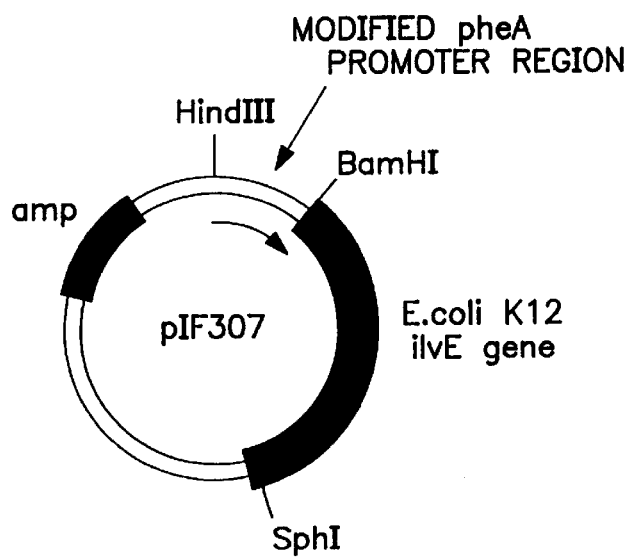
Figure 4:
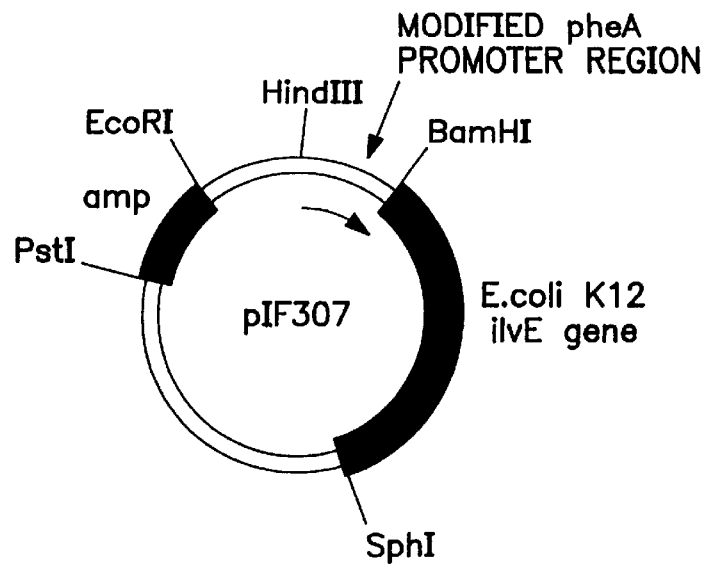
FIG. 4 shows the production of plasmid pIF312 from plasmid pIF307 discussed in Example 1 below.
Figure 4:
Figure 4:
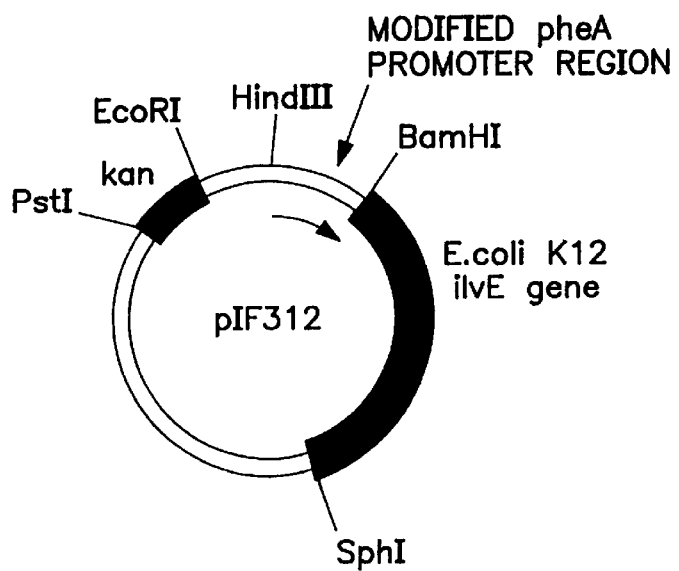
Figure 5:
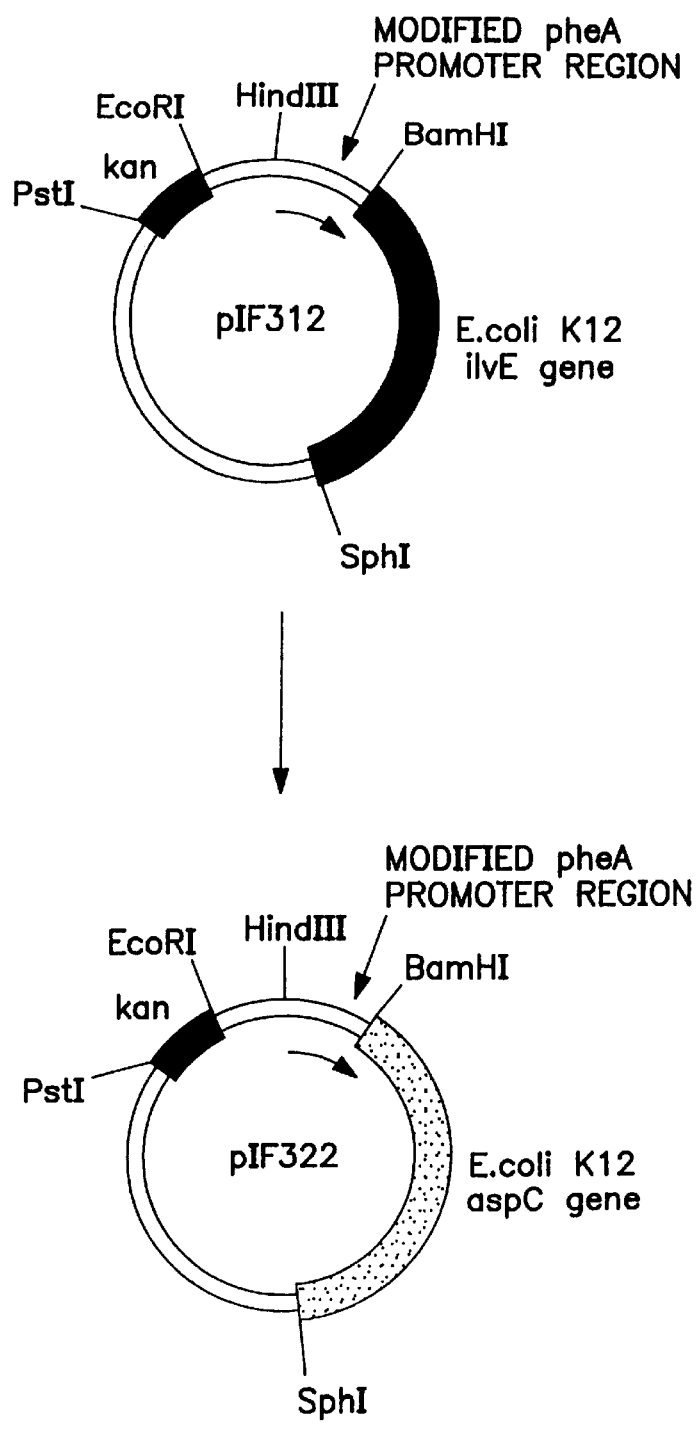
FIG. 5 shows the production of plasmid pIF322 from plasmid pIF312 discussed in Example 5 below.
Figure 6:
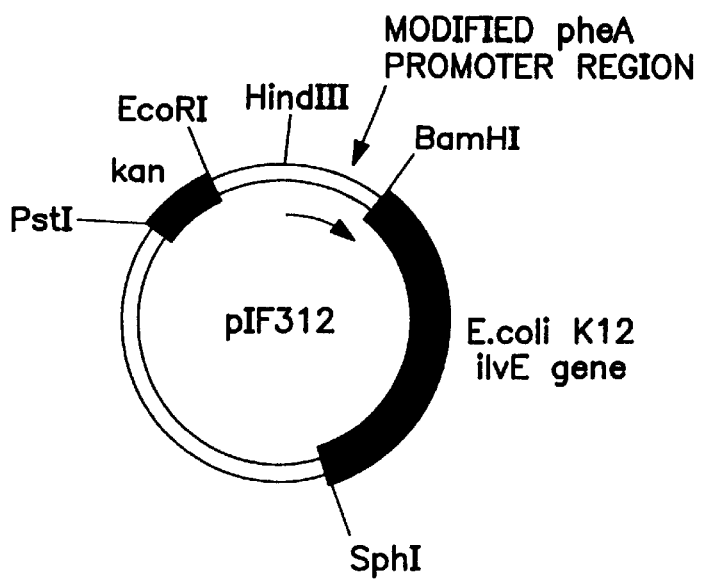
FIG. 6 shows the production of plasmid pIF347 from plasmid pIF312 discussed in Example 2 below.
Figure 6:
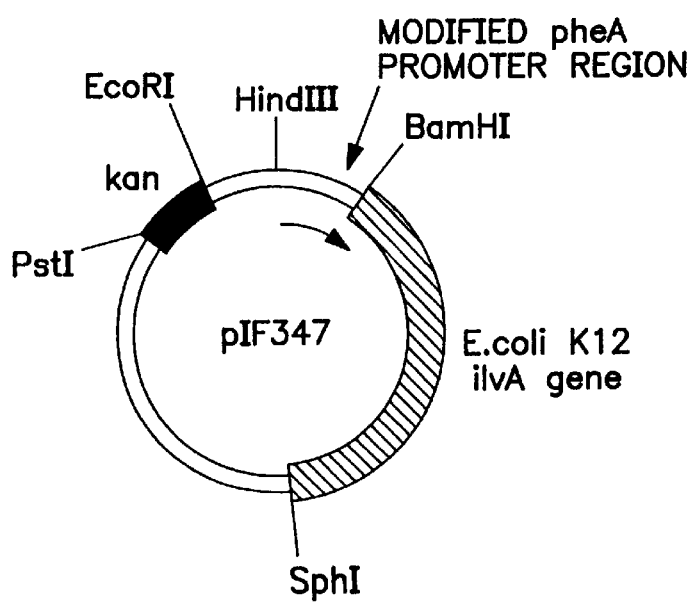
Figure 7:
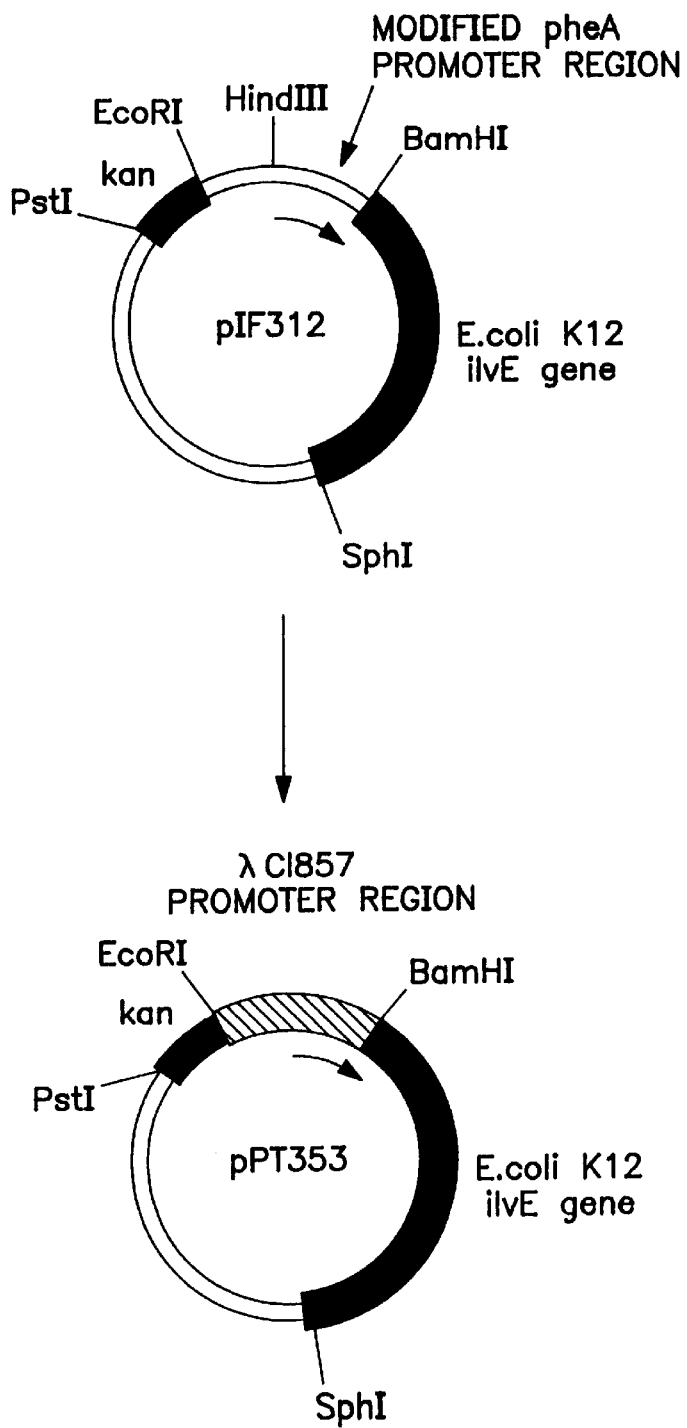
FIG. 7 shows the production of plasmid pPT353 from plasmid pIF312 discussed in Example 1 below.
Figure 8:
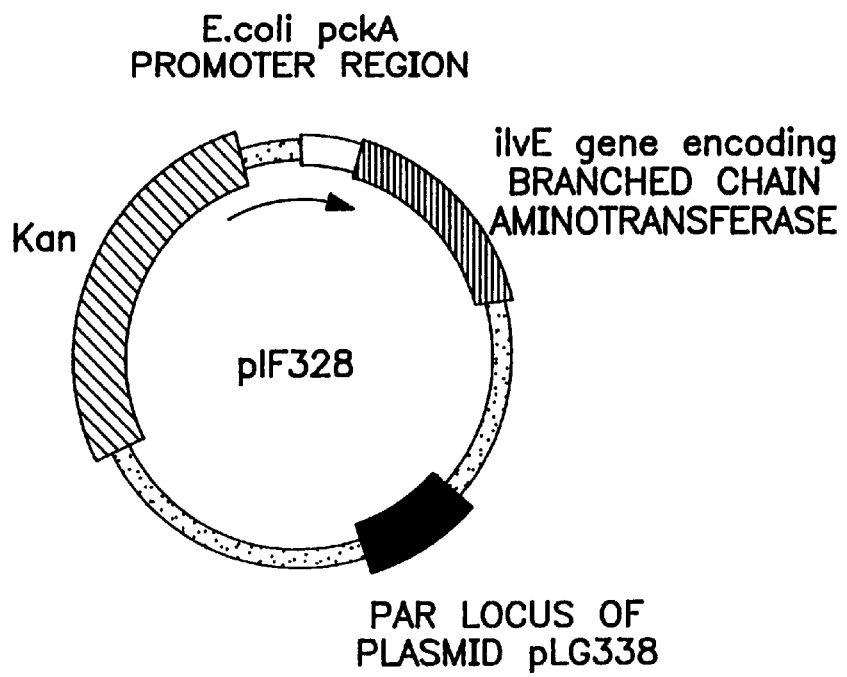
FIG. 8 shows plasmid pIF328 discussed in Example 7 below.
Figure 9:
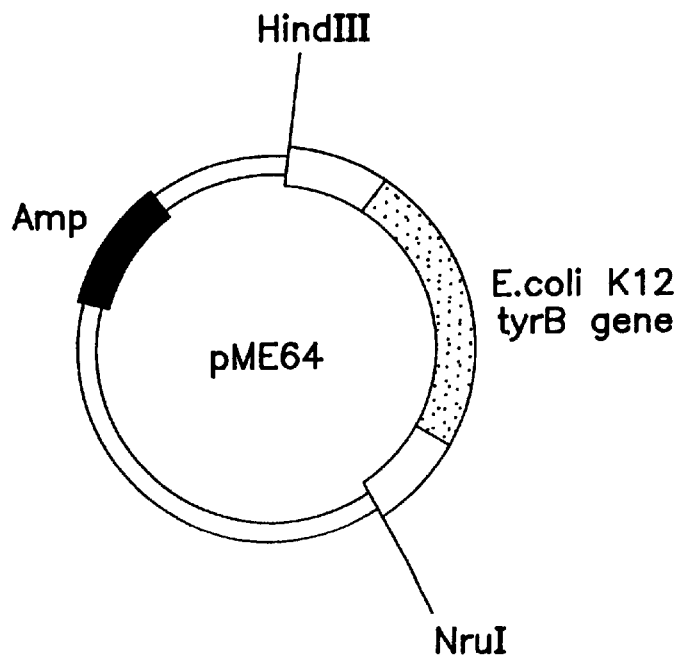
FIG. 9 shows plasmid pME64 discussed in Example 3 below.
Figure 10:
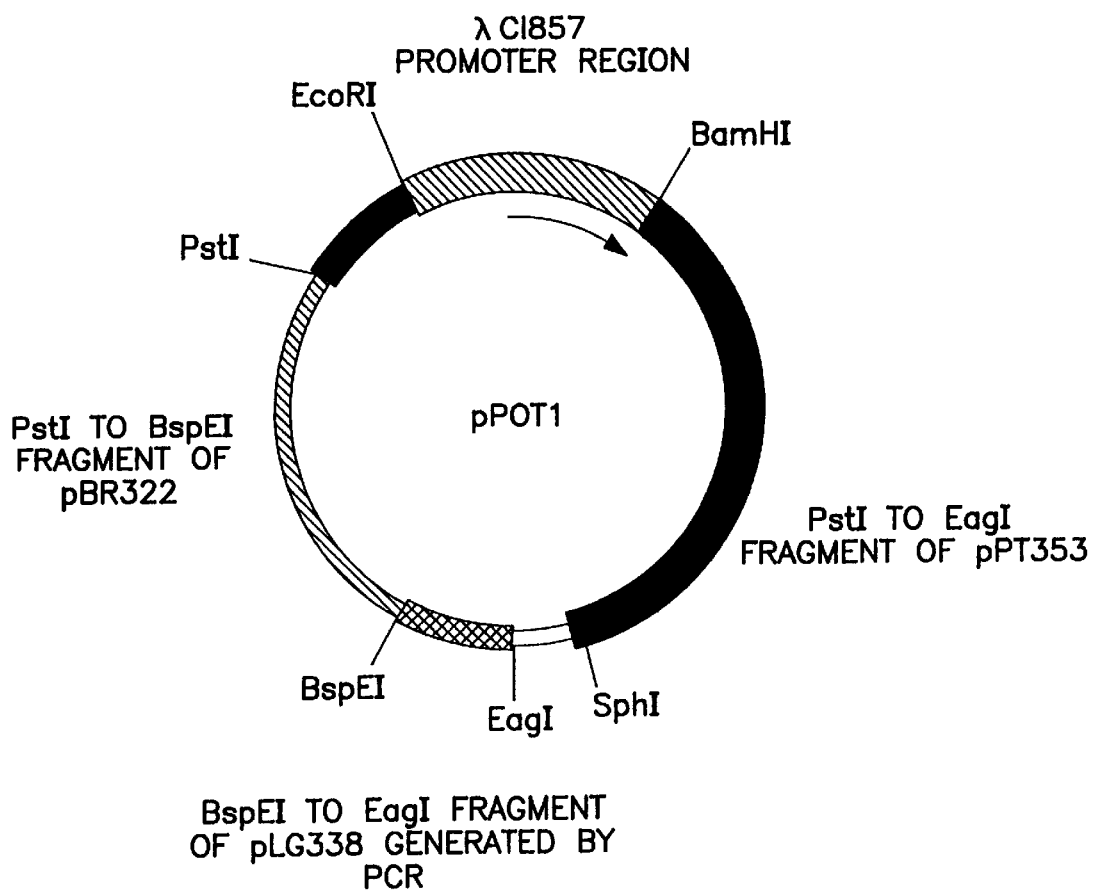
FIG. 10 shows plasmid pPOT1 discussed in Example 1 below.
Figure 11:
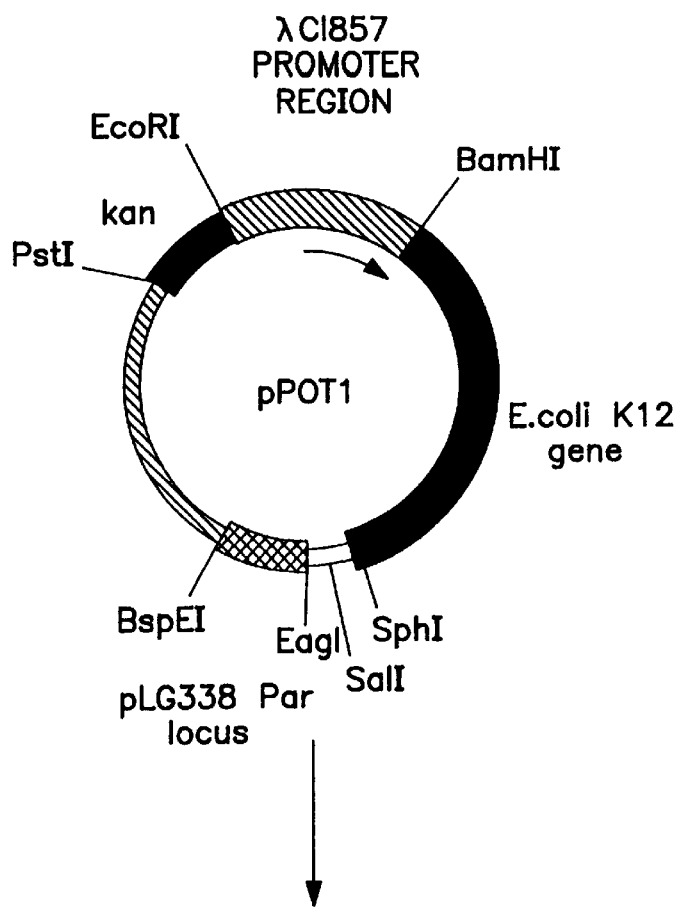
FIG. 11 shows the production of plasmid pPOT2 from plasmid pPOT1 discussed in Example 1 below.
Figure 11:
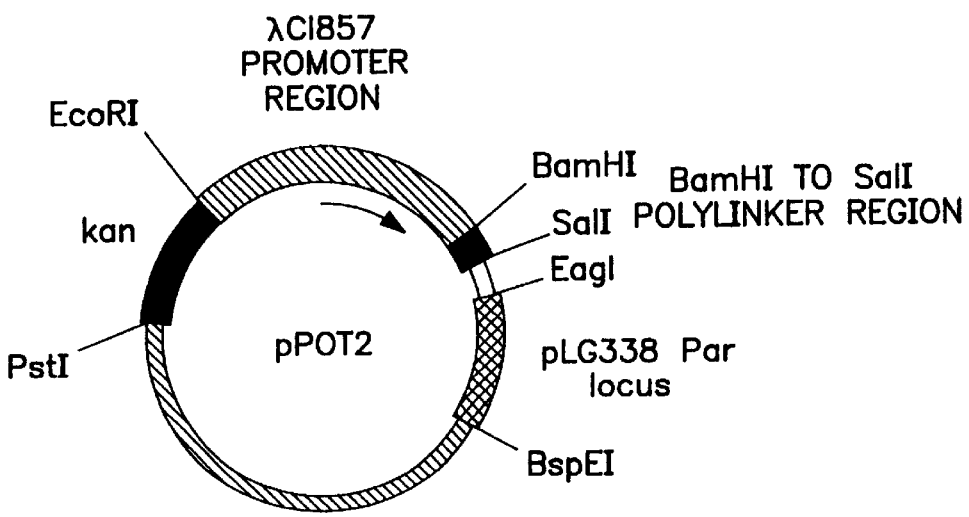
Figure 12:
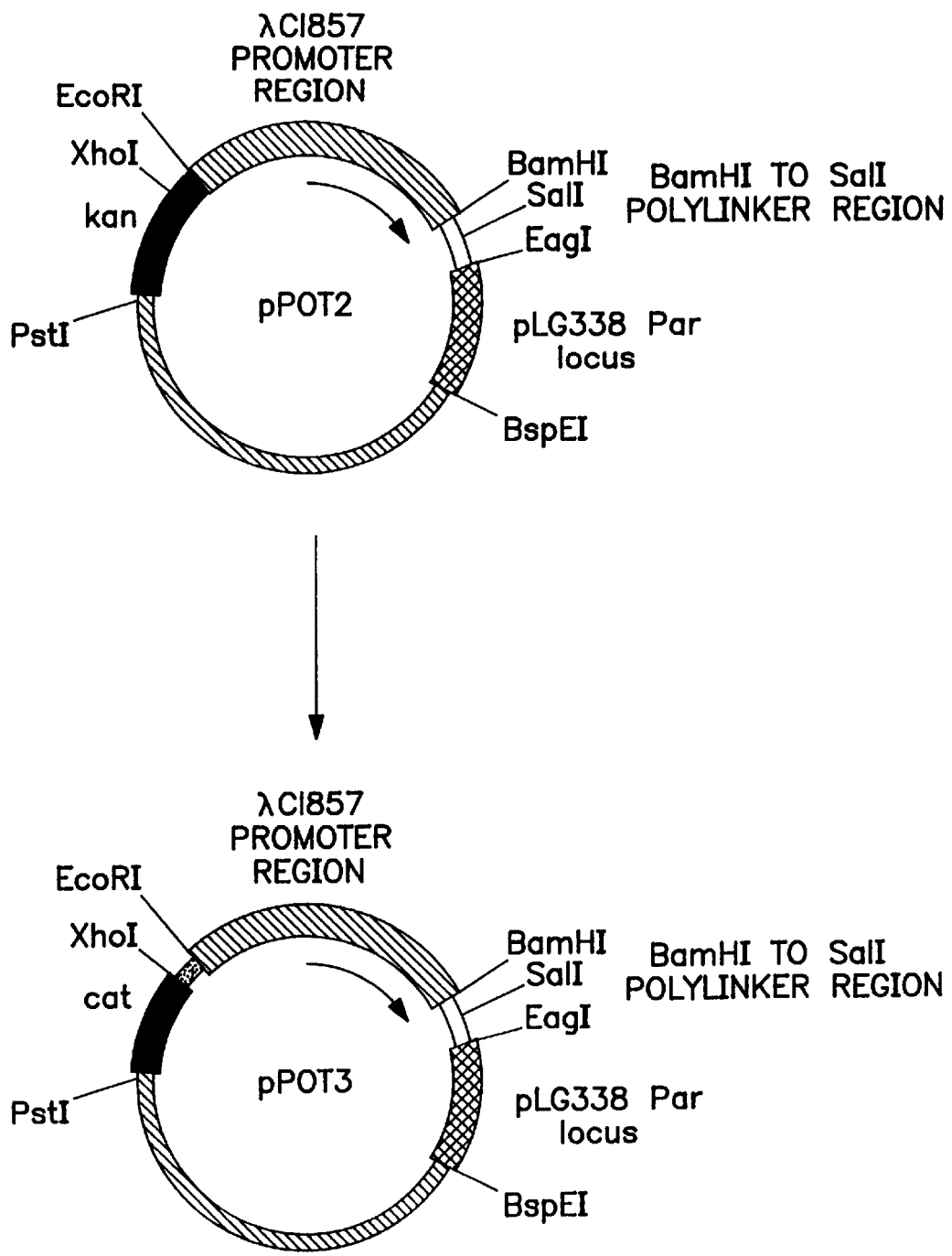
FIG. 12 shows the production of plasmid pPOT3 from plasmid pPOT2 discussed in Example 1 below.
Figure 13:
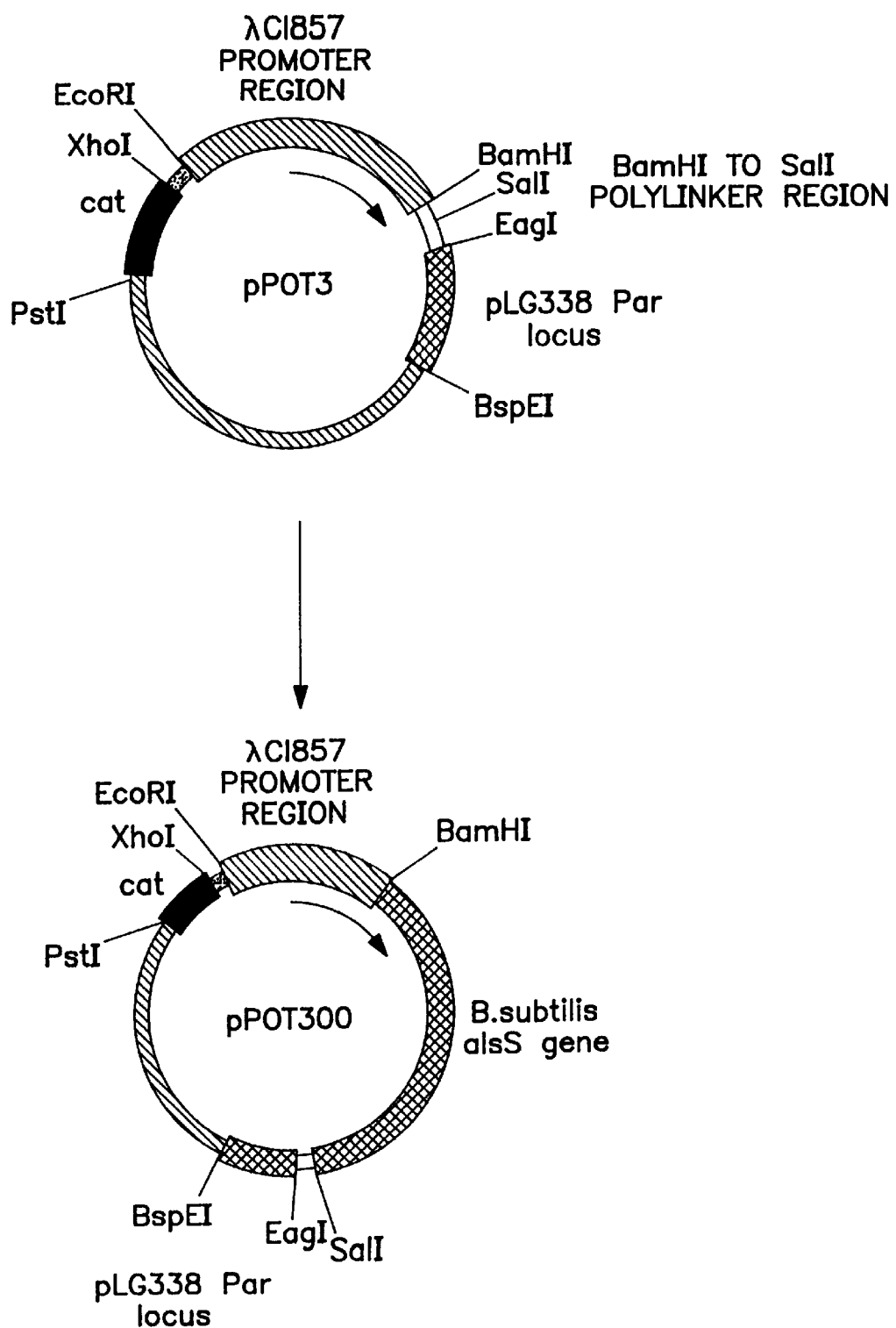
FIG. 13 shows the production of plasmid pPOT300 from plasmid pPOT3 discussed in Example 4 below.
Figure 14:
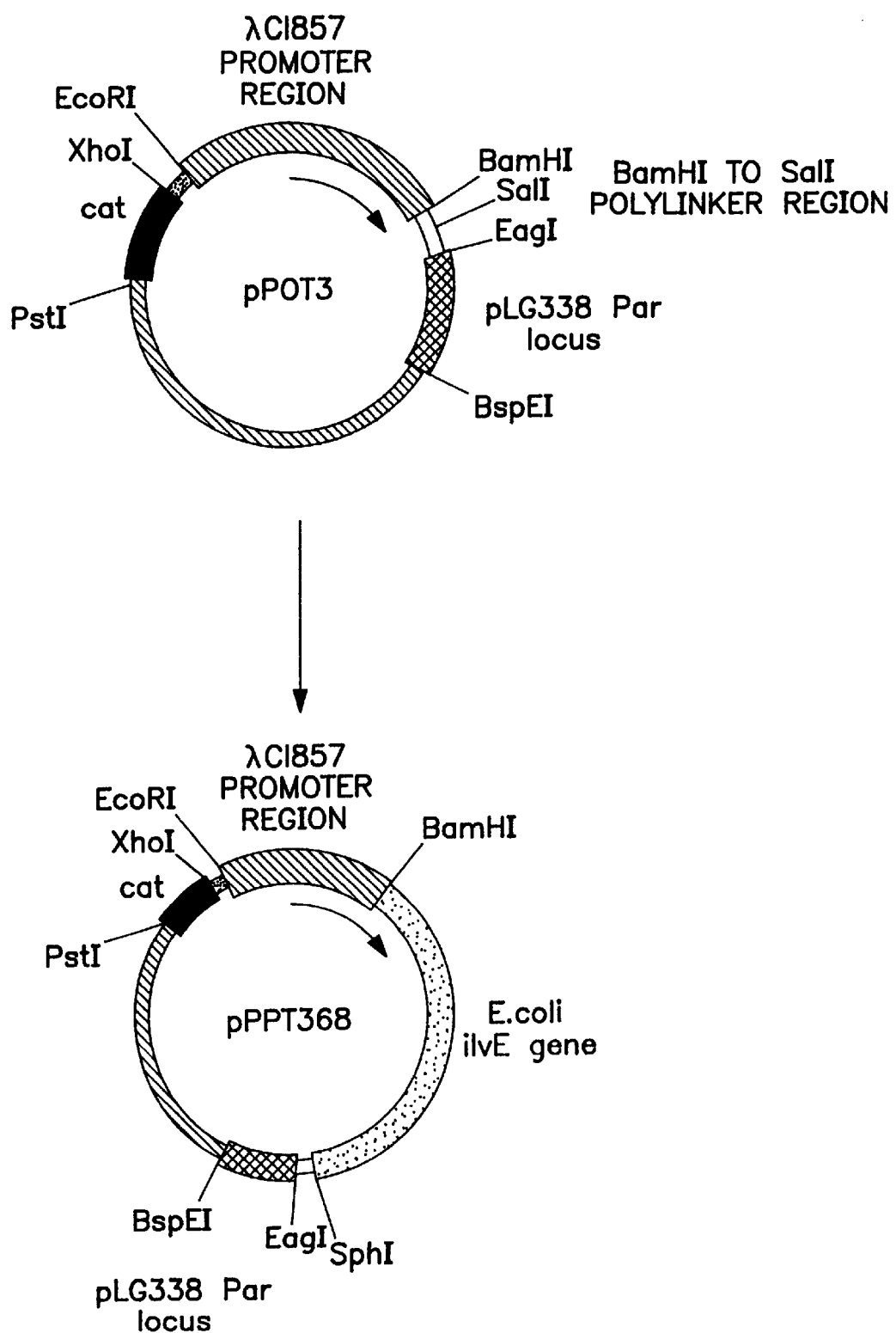
FIG. 14 shows the production of plasmid pPPT368 from plasmid pPOT3 discussed in Example 8 below.

This invention provides a process for making an amino acid which comprises reacting a first amino acid, a keto acid and a transaminase enzyme under conditions appropriate to produce a second amino acid and pyruvate; and reacting the pyruvate with acetolactate synthase under conditions appropriate to produce a compound that does not react with the transaminase enzyme.

The process of this invention is schematically described as follows:

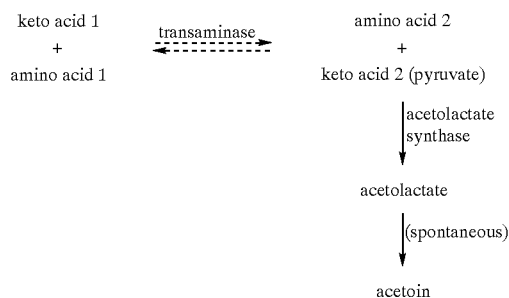

Scheme 1

In the practice of this invention the first amino acid, sometimes referred to herein as the "amino donor", includes any amino acid that will react with a transaminase and a keto acid, sometimes referred to herein as the "keto donor" to produce the desired amino acid product ("amino acid 2" in Scheme 1) and pyruvate ("keto acid 2" in Scheme 1). In one embodiment the first amino acid is alanine, which directly forms pyruvate under such conditions. See, Tokarski et al. In a preferred embodiment the first amino acid is L-aspartate. The transaminase reaction of a keto acid with L-aspartate produces oxaloacetate as the second keto acid. Contrary to the disclosure of Rozzell I, those of ordinary skill in the art recognize that under normal reaction conditions oxaloacetate undergoes a spontaneous loss of $CO_2$ to form pyruvate.

The process of this invention removes the pyruvate by the reaction of the second enzyme, acetolactate synthase, which condenses two molecules of the pyruvate to produce acetolactate. During the condensation the carboxyl group leaves as a molecule of carbon dioxide, rendering this reaction essentially irreversible. Acetolactate then undergoes a further spontaneous decarboxylation to produce acetoin, which is volatile and easy to separate from the amino acid product of the reaction using known techniques to afford a purified amino acid product if desired.

Transaminases with varying selectivities are known. See Transaminases, (1985); Amino Acids: Biosynthesis and Genetic Regulation (1983); and U.S. Pat. No. 4,826,766 (Rozzell II). The processes of the invention are intended to encompass the use of any natural or non-naturally occurring microorganism, such as a bacterium or virus, that produces transaminase enzymes. As used herein, the term "non-naturally occurring microorganism" is intended to include all genetically altered microorganisms that produce transaminase enzymes. For example, Rozzell II discloses several microorganism sources for transaminases having selectivities for aromatic amino acids, branched chain amino acids, and amino acids having acidic side chains.

In one embodiment of the process, the transaminase enzyme is produced by cells of a non-naturally occuring microorganism that contains a gene encoding a transaminase enzyme. For example, the gene encoding the transaminase can be incorporated into a plasmid that is inserted into a cell such that the cell produces the transaminase enzyme. In another embodiment of the invention a multiplicity of transaminase enzymes, for example 2, 3, 4, and the like, can be simultaneously utilized in the process. Thus, as used herein "transaminase enzyme" can comprise one or more than one transaminase enzymes being used simultaneously. In a preferred embodiment, whether as a single transaminase enzyme or as one of a multiplicity of transaminase enzymes, the transaminase enzymes used is the enzyme produced by plasmid pME64 described herein.

A general description of sources of acetolactate synthases can be found in Renna, M. C. et al., *J. Bacteriol.*, (1993) Vol. 175, pp. 3863–3875; and Wek, R. C. et al., *Nucleic Acids Res.*, (1985) Vol. 13, pp. 3995–4010. These references are hereby incorporated in their entirety into this specification by reference. As noted above for the transaminase enzyme, the processes of the invention are intended to encompass the use of any natural or non-naturally occurring microorganism, such as a bacterium or virus, that produces acetolactate synthase enzymes. In one embodiment of the process, the acetolactate synthase enzyme is produced by cells of a non-naturally occuring microorganism that contains a gene encoding a transaminase enzyme. For example, the gene encoding the acetolactate synthase can be incorporated into a plasmid that is inserted into a cell such that the cell produces the acetolactate synthase enzyme. In another embodiment of the invention a multiplicity of acetolactate synthase enzymes, for example 2, 3, 4, and the like, can be simultaneously utilized in the process. Thus, as used herein "acetolactate synthase enzyme" can comprise one or more than one acetolactate synthase enzymes being used simultaneously. In a preferred embodiment, whether as a single acetolactate synthase enzyme or as one of a multiplicity of acetolactate synthase enzymes, the acetolactate synthase enzyme is the enzyme produced by plasmid pPOT300 described herein.

The process of this invention can be applied to produce a variety of natural and non-naturally occurring amino acids simply by selecting the appropriate keto acid. See, U.S. Pat. No. 4,518,692 and Transaminases, (1985) for disclosures of a broad range of keto acids which are useful in this invention. In a preferred embodiment, the keto acid is 2-ketobutyrate. In a separately preferred embodiment, the keto acid is tri-methyl pyruvate.

In addition to these sources, keto donors can also be prepared from readily available starting materials, including other amino acids. For example, the enzyme threonine deaminase reacts with L-threonine to produce 2-ketobutyrate. See Scheme 2 below. The keto acid, thus produced, is then reacted with the L-aspartate amino acid substrate according to the process described above to produce L-2-aminobutyrate. L-threonine is a inexpensive starting material available from Archer Daniels Midland (Decatur, IL) and the reaction produces 2-ketobutyrate in essentially 100% yield. See, *Amino Acids: Biosynthesis and Genetic Regulation* (1983) cited above.

Scheme 2

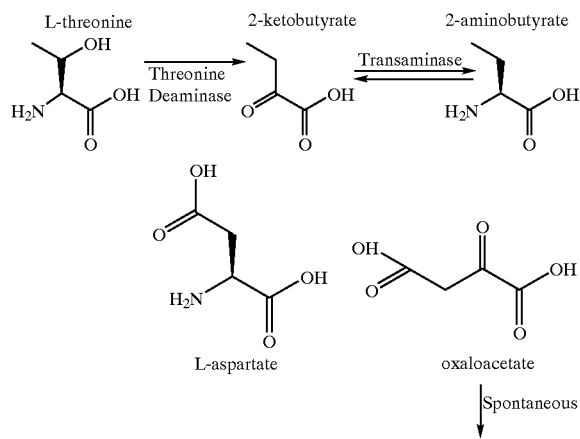

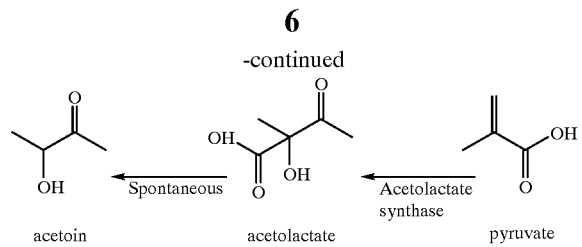

Additional reactions using various amino acid starting materials to produce various keto acids that are useful in this process are known in the art. *Gene*, (1989) Vol. 76, pp. 255–269 and *Gene*, (1988) Vol. 63, pp. 245–252 describe See also, Massad G., et al., *J.Bacteriol.*, (1992) Vol 177, pp. 5878–5883, for a general description of the activity of amino acid deaminase enzymes from Proteus mirabilis. These references are hereby incorporated in their entireties into this specification.

Thus, this invention also provides a process for producing an amino acid which comprises:
 a) reacting a first amino acid with an enzyme under conditions appropriate to produce a keto acid;
 b) reacting the keto acid with a second amino acid and a transaminase enzyme under conditions appropriate to produce a third amino acid and pyruvate; and
 c) reacting pyruvate with acetolactate synthase.

Reaction of the pyruvate in step (c) proceeds according to the description above to produce acetoin which can be readily separated from the third amino acid to isolate the amino acid product. In a preferred embodiment the enzyme is step (a) is a deaminase enzyme. In a particularly preferred embodiment the first amino acid is threonine and the enzyme is threonine deaminase.

In a preferred embodiment, the invention provides a process for producing 2-amino butyrate which comprises:
 a) reacting L-threonine with a threonine deaminase enzyme under conditions appropriate to produce 2-ketobutyrate;
 b) reacting 2-ketobutyrate with an amino acid and a transaminase enzyme under conditions appropriate to produce 2-aminobutyrate and pyruvate; and
 c) reacting pyruvate with acetolactate synthase.

In the practice of these methods the enzyme used in step (a), such as a deaminase, can be from any of the sources described above, or can be a multiplicity of enzymes as described above. In one embodiment of the invention a multiplicity of enzymes, for example 2, 3, 4, and the like, can be simultaneously utilized in the process. Thus, as used herein "deaminase enzyme" can comprise one or more than one deaminase enzymes being used simultaneously. In a preferred embodiment of this process the deaminase enzyme is a threonine deaminase enzyme produced by plasmid pIF347 described herein. In the practice of this method of the invention the amino acid and the transaminase enzyme used in step (b) can be any amino acid and transaminase enzyme as described above that form pyruvate. In a preferred embodiment the amino acid in step (b) is L-aspartate. In a separately preferred embodiment the transaminase enzyme is an enzyme produced by the plasmid pME64. The acetolactate synthase enzyme used in step (c) can be from any of the sources described above. In a preferred embodiment of the invention, the acetolactate synthase enzyme is the enzyme produced by the plasmid pPOT300.

Techniques for Utilizing Enzymes

In the practice of this invention "conditions appropriate" to react the described enzymes with the described substrates are known to those of ordinary skill in the art.

For example, cells producing transaminase and acetolactate synthase enzymes may be contacted with a solution containing the keto acid and amino acid starting materials with the resulting conversion of at least a portion of the keto acid starting material in the reaction mixture to the desired amino acid product. The cells may be permeabilized to facilitate diffusion of the substrates and products into and out of the cells. This permeabilization can be accomplished by treating cells with a low concentration of a surfactant, including but not limited to TWEEN 80, TRITON X-100, NONIDET P40, cetylpyridinium chloride, deoxycholic acid, hexadecyltrimethylammonium bromide or benzalkonium chloride. Further, organic solvents, including but not limited to N,N-dimethylformamide (DMF), dimethyl sulfoxide (DMSO), ethanol or acetone at low concentrations have also been used to increase permeabilization. Enzymes, including the transaminase, threonine deaminase, and the acetolactate synthase, may also be added to the starting reaction mixture in the form of cell extracts containing crude, partially purified, or purified enzyme. Cell extracts are prepared by methods known to those skilled in the art which provide for cell disruption and recovery of the enzyme. Cell disruption, can be accomplished by mechanical or non-mechanical means. Most often, for bacterial suspensions mechanical devices such as a French pressure cell, ultrasonication, bead mill or Manton-Gaulin homogenizer is used with the specifics of the method known to those of ordinary skill in the art. See, Scopes, R. K. "Protein Purification", (1982) (Springer-Verlag, New York). The reaction using the cell extract is then carried out in similar fashion to the whole cell method discussed above.

The enzyme-containing cells, or extracts thereof or purified enzyme or enzyme fractions, may also be immobilized, if desired. Immobilization methods which may be used in the practice of this invention include well-known methods such as entrapment in polymeric gels, covalent attachment, crosslinking, adsorption, and encapsulation. Some examples of these methods are described by A.M. Klibanov in Science, 219:722–727 (1983) and the references therein and in Methods in Enzymology (1976), Volume 44, (K. Mosbach editor) which are hereby incorporated by reference. In one method of immobilization disclosed in U.S. Pat. No. 5,019, 509, a support material containing at least 20% by weight of silica or alumina is contacted with aminoalkyl compound such as an aminoalkyl silane, polyethyleneimine, or a polyalkylamine, followed by activation with glutaraldehyde. The enzyme-containing solution is then contacted with the activated support to produce an immobilized enzyme composition having transaminase- and/or acetolactate synthase activity. Other immobilization supports useful in the practice of this invention include, but are not limited to, porous glass and porous ceramics, bentonite, diatomaceous earth, charcoal SEPHAROSE® and SEPHAROSE® derivatives, cellulose and cellulose derivatives, polyacrylamide and polyacrylamide derivatives, polyazetidine, alginate, carrageenan, and CHROMOSORB®. SEPHAROSE® (Pharmacia Fine Chemicals, Uppsala Sweden) is a bead-formed gel prepared from agarose. The manufacturer's product literature reports that in its natural state, agarose occurs as part of the complex mixture of charged and neutral polysaccharides referred to as agar. The agarose used to make SEPHAROSE® is obtained by a purification process which removes the charged polysaccharides to give a gel with only a very small number of residual charged groups. Those of ordinary skill in the art will appreciate that a number of other materials suitable for the immobilization of cells or extracts derived therefrom may also be useful for the immobilization of the enzymes usde in the present invention. These supports can be activated, if desired, by techniques well-known in the art.

The reaction to produce a desired amino acid product utilizing cells containing transaminase and acetolactate synthase, or compositions comprising extracts derived from said cells, is carried out by contacting a solution containing a first keto acid and a first amino acid with the enzymes under conditions permitting the conversion of at least a portion of the first keto acid to the desired amino acid. In the practice of the processes of this invention the cells contact an aqueous solution of the enzymes at a cell concentration in the range of about 50 mg/ml to about 200 mg/ml. In a prerrered embodiment the cell concentration is about 100 mg/ml. When the invention is practiced using extracts of cells, the extracts are prepared from an amount of cells that would give these cell concentrations.

The enzymatic reactions of this invention are carried out at temperatures in the range of from about 30° C. to about 50° C., and preferably at temperatures ranging from about 37° C. to about 45° C. The optimal pH for the reaction ranges from about 6 to about 9, and more preferably from about 7 to about 8, with a pH of 8 being most preferred.

The invention will now be further illustrated by the following examples, which are not intended, and should not be interpreted, to limit the scope of the invention which is defined in the claims which follow thereafter.

Experimental Details

Examples 1–4 show the production of plasmids containing genes which encode for the preferred enzymes used in a preferred embodiment of the process of the claimed invention, the production of L-2-aminobutyrate. In the Examples these plasmids, pIF347, pME64, and pPOT300, were used separately in individual bacterial host strains, each utilizing host strain W3110. W3110 is obtained from the ATCC 10801 University Boulevard, Manassas, Va. 20110-2209 (ATCC Accession No. 27325). However, those of ordinary skill in the art will recognize that other individual host strains will be appropriate in the practice of this invention. In addition, those of ordinary skill will recognize that more than one or all plasmids can be incorporated into a single host strain and utilized as described above.

General molecular biology techniques known to those of ordinary skill in the art are used throughout. See, for example, *Molecular Cloning*, Sambrook et al. eds. (Second ed. 1989) (Cold Spring Harbor Publications, NY). PCR methods were carried out using a Perkin Elmer GENEAMP kit supplied by Roche (Branchburg, N.J.) according to the instructions supplied. Ligations were performed using a kit supplied by Takara Biochemical (Pan Vera Corp., Madison, Wis.) according to the instructions supplied. DNA cleavages were performed using restriction enzymes supplied by New England Biolabs (Beverly, Mass.) according to the instructions supplied. Chromosomal DNA was prepared using Qiagen genomic DNA kits (Qiagen, Santa Clarita, Calif.) according to the instructions supplied. Qiagen further supplied PCR purification kits, which were used according to the instructions supplied.

The expression of the genes was carried out on a series of expression vectors that represent a preferred embodiment of the invention, and which are referred to herein as pPOT. These plasmids enable one to turn on the production of the enzymes at a particular stage in the growth of the cells by adjusting the temperature of the fermentor. The plasmids carry a mutated version of a repressor named cI from phage lambda. See, *Lambda II*, R. W. Hendrix et al., eds. (1983) (Cold Spring Harbor Publications, NY); and Stratagene Cloning Systems Product Catalog (Stratagene Cloning Systems, La Jolla, Calif.). The mutation makes the repressor unstable at elevated temperatures such as those above about 30° C. The repressor normally prevents expression of genes under control of the promoter $P_R$. When the temperature is raised the repressor becomes inactive and the promoter begins to work. In each case the gene of interest is placed under control of the promoter $P_R$.

EXAMPLE 1

Construction of the Expression Vectors pPOT1, pPOT2 and pPOT3

Plasmid pPOT1. Plasmid pBR322 was obtained from New England Biolabs (Beverly, Mass.). A modified pheA promoter was inserted between unique HindIII and SphI sites on pBR322 to construct pIF306. Within the HindIII to SphI insert there exists unique BamHI and BqlII sites. The modified pheA promoter was derived from that characterized in co-owned U.S. Pat. No. 5,120,837 to Fotheringham et al. which is incorporated by reference herein, such that the sequence was as follows:

HindIII
AAGCTTTTTGTTGACAGCGTGAAAA-CAGTACGGGTATAATACT AAAGTCACAAG-GAGGATCCACTATGACATCGGAAAAC-CCGTTACT GGCGCT
HaeII (SEQ ID NO. 1)

pIF306 was cleaved with the enzymes BamHI and SDhI. The 3.9 kB fragment was isolated and ligated to a similarly cleaved fragment containing the *E. coli* K12 ilvE gene which was generated by PCR from W3110 chromosome using the following oligonucleotide primers:

5' CGC GGA TCC ACT ATG ACC ACG AAG AAA GCT GAT TAC ATT TGG 3' (SEQ. ID NO. 2)

5' CAG CGT GCA TGC TTA TTG ATT AAC TTG ATC TAA CCA GC3' (SEQ. ID NO. 3)

The resulting vector was named pIF307. Plasmid pIF307 was cleaved with enzymes EcoRI and PstI and the 4.1 kB fragment isolated. This was ligated to a similarly cleaved and purified 982 base pair DNA fragment containing the kanamycin resistance gene from plasmid pLG338 (pLG338 is described in U.S. Pat. No. 5,120,837 and Stoker et al Gene 18:, 335–341). This was generated using PCR with the following oligonucleotide primers:

5' CCG GAA TTC ACG TTG TGT CTC AAA ATC TCT GAT 3' (SEQ. ID NO. 4)

5' CCG CTG CAG GCC GTC CCG TCA AGT CAG CGT AAT G 3' (SEQ. ID NO. 5)

The resulting plasmid was named pIF312. Plasmid pIF312 was cleaved by EcoRI and BamHI and the resulting 4.97 kB fragment was ligated to the phage lambda cI857 gene which was similarly cleaved following isolation by PCR using the Lambda ZapII vector (Stratagene, La Jolla, Calif.) as template and the following oligonucleotide primers:

5' TTTGGATCCTCCTTAGTACATGCAACC 3' (SEQ. ID NO. 6)

5' TTTGAATTCGGATGAAGATTCTTGCTCGATTGT 3' (SEQ. ID NO. 7)

The resulting plasmid was named pPT353. This plasmid was then cleaved with PstI and EagI and the 3.17kB fragment was isolated. Plasmid pPOT1 can then be constructed by ligating this fragment to the 1.95kB PstI to BspEI fragment of pBR322 and the PCR fragment generated from pLG338 using the oligonucleotides:

5' GGC GGC CGA CGC GCT GGG CTA CG 3' (SEQ. ID NO. 8)

5' CCC TCG CAA GCT CGT CCG GAG GCA AAT CGC TGA ATA TTC C 3' (SEQ. ID NO. 9)

This PCR results in the amplification of a 0.59kB DNA fragment. This fragment is then cleaved with BspEI and EagI to generate the necessary sticky ends for the trimolecular ligation to generate pPOT1.

To generate plasmid pPOT2, pPOT1 was then cleaved with BamHI and SalI and the 4.68 kB fragment isolated. This fragment was ligated to an oligonucleotide linker prepared by annealing the following two oligonucleotides:

5' GATCCTAGGTACCGGTGCGGCCGCAT-GCTGACTGACTGAAGATCCCGGGCGATTCT ACGC-CCGGGTTTTTATG 3' (SEQ. ID NO. 10)

5' TCGACATAAAAACCCGGGCGTA-GAATCGCCCGGGATCTTCAGTCAGTCAGCATGC GGCCGCACCGGTACCTAG3' (SEQ. ID NO. 11)

The resulting plasmid was named pPOT2. This plasmid was cleaved with XhoI and PstI and the 3.9 kb fragment isolated. This was ligated to a fragment similarly cleaved with XhoI and PstI containing the cat gene of HSG415 described in U.S. Pat. No. 5,345,672 (Fotheringham), the disclosure of which is hereby incorporated into this specification by reference. The cat gene confers chloramphenicol resistance upon the host strain and can be isolated form plasmid HSG415 using the following oligonucleotide primers:

5' GAC CTC GAG GCA CTT TGC GCC GAA TAA ATA CCT GTG 3' (SEQ. ID NO. 12)

5' GAC CTG CAG CAC CAG GCG TTT AAG GGC ACC AAT AAC 3' (SEQ. ID NO. 13)

The resulting plasmid was named pPOT3.

EXAMPLE 2

Plasmid pIF347 Comprising the *E. coli* ilvA Gene Encoding Threonine Deaminase

To construct pIF347 the ilvA gene encoding threonine deaminase was amplified from the chromosome of *E. coli* K12 by PCR. *E. coli* K12 chromosomal DNA was prepared using standard methodology. The ilvA gene was specifically amplified by PCR using the oligonucleotide primers:

5' CGC GGA TCC ATC ATG GCT GAC TCG CAA CCC C 3' (SEQ. ID NO. 14)

5' CTC GCA TGC CAG GCA TTT TTC CCT AAC CCG CC 3' (SEQ. ID NO. 15)

The PCR product was cleaved using the restriction enzymes BamHI and SphI and the 1.57kB fragment thus generated was ligated to the 4.1 kB fragment of pIF312 which had been similarly cleaved with BamHI and SphI.

The resulting plasmid was named pIF347.

EXAMPLE 3

Plasmid pME64 Comprising the *E. coli* tyrB Gene Encoding Tyrosine Aminotransferase Plasmid pME64, which contains a fragment of the *E. coli* K12 chromosome encoding the tyrb gene, is described in Fotheringham et al., *Biochemical Journal*, (1986) Vol. 234, pp. 593–604, the contents of which are hereby incorporated into this specification by reference. The tyrB gene may also be isolated directly from the chromosome of *E. coli* K12 using oligonucleotide primers based on the sequence disclosed in the reference using standard techniques.

EXAMPLE 4

Plasmid pPOT300 Comprising the *B. subtilis* alsS Gene Encoding Acetolactate Synthase The alsS gene was amplified from the *B.subtilis* chromosome using PCR. *B.subtilis* chromosomal DNA was prepared using the same procedure as for *E. coli* K12. The alsS gene was specifically amplified by PCR using the following oligonucleotide primers.

5' TTT GAA TCC ATC ACA AGA TAT TTA AAA TTT 3' (SEQ. ID NO. 16)

5' TTT AGC GTC GAC GCA TGC TCC TTT TAT TTA GTG CTG TTC 3' (SEQ. ID NO. 17)

The PCR product was then cleaved with the enzymes BamHI and SalI and the resulting 1.9 kB fragment was ligated to the 4.76 kB fragment of pPOT3 which was isolated by agarose gel electrophoresis following similar cleavage by BamHI and SalI. The resulting plasmid was named pPOT300. Plasmid pPOT300 was deposited with the ATCC (10801 University Blvd. Manassas, Va. 20110-2209, USA) under the terms of the Budapest Treaty and is assigned Patent Deposit Designation PTA-1694.

EXAMPLE 5

Construction of Plasmid pIF322

The aspC gene is also described in the publication Fotheringham et al., (1986). Based upon the sequence disclosed in this publication, the coding sequence of the gene can be isolated from the chromosome of *E. coli* K12 as a 1.2 kb fragment by PCR using the following oligonucleotide primers:

5' CGC GGA TCC ACT ATG TTT GAG AAC ATT ACC GCC 3' (SEQ. ID NO. 18)

5' CAG CGT GCA TGC TTA CAG CAC TGC CAC AAT CGC 3' (SEQ. ID NO. 19)

To construct pIF322, plasmid pIF312 was cleaved with BamHI and SphI and the 4.1 kb fragment isolated as before. This was ligated to the aspC containing PCR fragment to give pIF322.

EXAMPLE 6

Construction of Plasmid pIF349

Based upon the sequence disclosed in the Fotheringham (1986), the aspC gene along with the wild type promoter region can be isolated using as a 1.6 kb fragment by using the following oligonucleotide primers:

5' GAC GGA TTC CCA GAG CAA TCT CAC GTC TTG C 3' (SEQ. ID NO. 20)

5' GAC AGA TCT CCC TGA TAA GCG TAG CGC ATC AGG 3' (SEQ. ID NO. 21)

Following purification of the PCR product using a Qiagen PCR purification kit and digestion with EcoRI and BglII, the fragment can be ligated to the 7.1 kb EcoRI to BamHI fragment of plasmid pLG338. Plasmid pLG338 is described in U.S. Pat. No. 5,120,837 and and in Stoker et al., Gene Vol. 18, pp. 335–341, the contents of which are hereby incorporated into this specification by reference. The resulting plasmid is pIF349.

EXAMPLE 7

Construction of Plasmid pIF328

Plasmid pIF328 is derived from pIF312. Initially the pheA derived promoter region of pIF312 was replaced by one which was derived from the pckA promoter of *E. coli* K12. This is described in the GENBANK entry ECOPCKA. The pckA promoter was amplified on a 270 bp fragment using the following oligonucleotide primers:

5' GAC GAA TTC ACT TTA CCG GTT GAA TTT GC 3' (SEQ. ID NO. 22)

5' GAC GGA TCC TCC TTA GCC AAT ATG TAT TGC 3' (SEQ. ID NO. 23)

A mutation was introduced in the −10 region of the pcka promoter using standard PCR based mutagenesis procedures such that the wild type −10 sequence of 5' GATAAT 3' was changed to 5' TATAAT 3'. This resulted in the elimination of the normal catabolite repression of the promoter.

The fragment was isolated and purified using a Qiagen PCR purification kit and ligated to the 4.97 kb fragment of pIF312 generated by cleavage with EcoRI and BamHI. The resulting plasmid was pIF313.

Plasmid pIF313 was then cleaved with the enzymes BspEI and SphI and the 4.14 kb fragment isolated and purified using a Qiagen PCR purification kit. The Par, partition locus of pLG338 was then amplified by PCR using the following oligonucleotide primers:

5' CTT GCA TGC ACC ATT CCT TGC GGC GGC 3' (SEQ. ID NO. 24)

5' AGA TCC GGA GGC AAA TCG CTG AAT ATT CC 3' (SEQ. ID NO. 25)

The resulting 970 bp fragment was cleaved with BspEI and SphI and ligated to the pIF313 fragment. The resulting plasmid was pIF328.

EXAMPLE 8

Construction of Plasmid pPT368

To construct pPT368, plasmid pPOT3 was cleaved by the enzymes BamHI and SphI and the 4.8 kb fragment isolated. The *E. coli* K12 ilvE gene was amplified from the *E. coli* chromosome by PCR using the following oligonucleotide primers:

5' CGC GGA TCC ACT ATG ACC ACG AAG AAA GCT GAT TAC ATT TGG 3' (SEQ. ID NO. 26)

5' CAG CGT GCA TGC TTA TTG ATTAAC TTG ATC TAA CCA GC 3' (SEQ. ID NO. 27)

This 0.94 kb fragment was purified using a Qiagen PCR purification kit, similarly cleaved with BamHI and SphI and ligated to the fragment of pPOT3. The resulting plasmid was pPT368.

In the following Examples 9 and 10 the effect of acetolactate synthase upon the efficiency of 2-aminobutyrate biosynthesis was investigated using 2-ketobutyrate or L-threonine as substrate. Cell cultures of W3110 cells carrying pME64, pPOT300 or pIF347 were prepared by inoculating 50 mls of LB medium with a single colony from an LB agar plate and culturing overnight at 37° C. in an 500 ml flask in a shaking incubator. Antibiotics, where appropriate, were added at the concentrations of 100 µg/ml ampicillin, 40µg/ml kanamycin and 10 µg/ml chloramphenicol. The plasmid descriptions from the Examples above show which antibiotic is required by each plasmid. Overnight cultures were then used to inoculate 1 liter of LB plus appropriate antibiotics to an initial OD600 of 0.05. These were grown at 37° C. in a 4 litre flask with agitation at 300 pm until the OD600 reached 1.0. The cells were then recovered by centrifugation at 10,000 G for 5 minutes washed in 50 mM Tris HCl buffer and similarly pelleted. The required weight of pelleted wet cells was then added to bioconversion mixes.

HPLC analysis for amino acids were carried out as follows.

1. L-2-aminobutyrate:

Methods: OPA/BOC-Cys derivatization.
Mobile Phase: Gradient method, Pump A=60% MeOH, 40% 0.05M TEAP, buffer pH=7.0; Pump B=H$_2$); Pumb B 32% at 0 min. and at 6 min., 5% by 8 min. At 14.1 min. revert to starting conditions.
Oven 40° C.
Column: Supelcosil LC-18DB, 3μ, 150=4.6 mm
Flow rate: 1.0 ml/min
Detection: UV @ 338 nm
Injection Volume: 10 μl
2. L-tert-leucine:
Methods: OPA/BOC-Cys derivatization.
Mobile Phase: Stock solution 300 mM NaHPO$_4$, pH 7.0; 11.635 g NaH$_2$PO$_4$ and 30.723 g Na$_2$HPO$_4$ dissolved in 1L water; Pump A=15 mM NaHPO$_4$; 50 ml stock diluted to 1L with water; Pump B=900ml of Pump A solution and 1100 ml of ACN.
Column: Supelcosil LC-18DB, 3μ, 150×4.6 mm
Flow rate: 1.5 ml/min
Detection: UV @ 338 nm
Injection Volume: 10 μl

EXAMPLE 9

Biosynthesis of 2-aminobutyrate Using 2-ketobutyrate as Substrate

The reaction was run using the following substrate concentrations:
Reaction A
Reaction volume 2 ml 2-ketobutyrate 500 mM (Adjusted to pH 7.5 with NaOH)
L-aspartic acid 500 mM (Adjusted to pH 7.5 with NaOH)
100 mM Tris pH 7.5
Reaction time 24 hrs 100 mg/ml Cells of W3110 containing pME64
Reaction B
Reaction volume 2 ml
2-ketobutyrate 500 mM (Adjusted to pH 7.5 with NaOH)
L-aspartic acid 500 mM (Adjusted to pH 7.5 with NaOH)
100 mM Tris pH 7.5
Reaction time 24 hrs
100 mg/ml cells of W3110 containing pME64 and 50 mg/ml cells of W3110 containing pPOT300

Following incubation for 24 hrs a 200 μl sample was taken from each reaction and the cells removed by centrifugation. The sample was then diluted 100 fold and subjected to amino acid analysis by HPLC according to the methods described above.

In the following Tables "L-2-aba" refers to L-2-amino butyrate, "L-ala" refers to content of L-alanine, "L-asp" refers to L-aspartic acid and "L-thr" refers to L-threonine, "L-t-leu" refers to content of L-tert-leucine, "L-glu" refers to content of L-glutamic acid. All content values in the Tables are in mg/ml.

TABLE 1

| Reaction | L-2-aba | L-ala | L-asp |
|---|---|---|---|
| A | 23.89 | 9.62 | 1.16 |
| B | 30.04 | 1.65 | 1.28 |

EXAMPLE 10

Biosynthesis of 2-aminobutyrate Using L-threonine as Substrate

The reaction was run using the following substrate concentrations:
Reaction A
Reaction volume 2 ml
L-threonine 500 mM (Adjusted to pH 8.0 with NaOH)
L-aspartic acid 500 mM (Adjusted to pH 8.0 with NaOH)
Reaction time 20 hrs
100 mg/ml cells of W3110 containing pME64
50 mg/ml cells of W3110 containing pIF347
Reaction B
Reaction volume 2 ml
L-threonine 500 mM (Adjusted to pH 8.0 with NaOH)
L-aspartic acid 500 mM (Adjusted to pH 8.0 with NaOH)
Reaction time 20 hrs
100 mg/ml cells of W3110 containing pME64
50 mg/ml cells of W3110 containing pIF347 and 50 mg/ml
  cells of W3110 containing pPOT300

Following incubation for 24 hrs a 200 μl sample was taken from each reaction and the cells removed by centrifugation. The sample was then diluted 100 fold and subjected to amino acid analysis by HPLC.

TABLE 2

| Reaction | L-2-aba | L-ala | L-asp | L-thr |
|---|---|---|---|---|
| A | 25.05 | 10.60 | 0.69 | und. |
| B | 27.71 | 1.23 | 1.01 | und. |

"Und" represents not detected.

The results show that the use of acetolactate synthase results in very significantly less accumulation of L-alanine in the biotransformation. This is true for biotransformations using either 2-ketobutyrate or L-threonine as the keto acid source.

In the case of 2-ketobutyrate the yield and relative purity are:

TABLE 3

|  | L-2-aba yield from substrate | L-2-aba/L-alanine ratio |
|---|---|---|
| − alsS | 46.4% | 2.4:1 |
| + alsS | 58.3% | 18.2:1 |

In the case of L-threonine the yield and relative purity are:

TABLE 4

|  | L-2-aba yield from substrate | L-2-aba/L-alanine ratio |
|---|---|---|
| − alsS | 46.4% | 2.4:1 |
| + alsS | 53.8% | 22.5:1 |

In each case the yield of product is improved to a moderate degree and the 2-aba:alanine ratio is dramatically improved roughly sevenfold and tenfold.

Although in these examples the genes were each present on a different plasmid in independent strains, it would be a logical step to combine the genes on one or more plasmids in a single strain. This would reduce the time, complexity and cost of fermenting the organisms for large scale manufacture of L-2-aba or other amino acids using this approach. In addition, those of ordinary skill in the art will recognize that separate genes encoding for more than one transaminase, deaminase and/or acetolactate synthase enzyme can be incorporated onto a single plasmid.

EXAMPLE 10

Comparative Example

Biosyntheses of L-tert-leucine Using Coupled transaminases With and Without alsS The following reaction provides a comparison of the claimed methods with process disclosed in Rozzell I patent discussed above.

Reaction A
Reaction volume 1 litre
Tri-methyl pyruvate 500 mM
L-aspartic acid 550 mM
L-glutamic acid 50 mM
pH 8.0
Reaction time 48 hrs
100 mg/ml cells of W3110 containing pIF349 and pPT368
Reaction B
Reaction volume 1 litre
Tri-methyl pyruvate 500 mM
L-apartic acid 550 mM
L-glutamic acid 50 mM
pH 8.0
Reaction time 48 hrs
100 mg/ml Cells of W3110 containing pIF328
50 mg/ml Cells of W3110 containing pIF322
50mg/ml Cells of W3110 containing pPOT300

Following incubation for 48 hours a 1 ml sample was taken from each reaction and the cells removed by centrifugation. The sample was then diluted 100 fold and subjected to amino acid analysis by HPLC.

TABLE 5

| Reaction | L-t-leu | L-ala | L-asp | L-glu |
|---|---|---|---|---|
| A | 43.9 | 11.6 | 0.0 | 5.7 |
| B | 48.1 | 6.0 | 1.5 | 5.6 |

These results show that the reaction as described in the Rozzell I, patent although showing complete conversion of the amino donor to product, does lead to the accumulation of alanine as a contaminating amino acid. Also, the addition of acetolactate synthase enzyme in the reaction leads to a reduction of alanine biosynthesis. The result can be expressed as a ratio of L-tert-leucine to L-alanine. In Reaction A (−alsS) the ratio is 3.78. In Reaction B (+alsS) the ratio is 8.02.

---

What is claimed is:

1. A process for making an amino acid which comprises reacting a first amino acid, and a keto acid with transaminase enzyme under conditions appropriate to produce a second amino acid and pyruvate; and reacting the pyruvate with acetolactate synthase enzyme under conditions appropriate to produce a compound that does not react with transaminase enzyme.

2. The process of claim 1 further comprising the step of isolating the second amino acid.

3. The process of claim 1 wherein the compound that does not react with transaminase enzyme is acetolactate.

4. The process of claim 1 wherein the compound that does not react with transaminase enzyme is acetoin.

5. The process of claim 1 wherein the first amino acid is alanine.

6. The process of claim 1 wherein the first amino acid is L-aspartate.

7. The process of claim 1 wherein the keto acid is 2-ketobutyrate.

8. The process of claim 1 wherein the keto acid is tri-methyl pyruvate.

9. The process of claim 1 wherein transaminase enzyme is present in aqueous solution as whole cells producing transaminase enzyme.

10. The process of claim 1 wherein transaminase enzyme is present in aqueous solution as cell extracts of whole cells producing transaminase enzyme.

11. The process of claim 1 wherein transaminase enzyme is present as immobilized enzyme.

12. The process of claim 1 wherein transaminase enzyme is produced by a non-naturally occurring microorganism comprising a DNA coding sequence that encodes for transaminase enzyme.

13. The process of claim 1 wherein acetolactate synthase enzyme is present in aqueous solution as whole cells producing acetolactate synthase enzyme.

14. The process of claim 1 wherein acetolactate synthase enzyme is present in aqueous solution as cell extracts of whole cells producing acetolactate synthase enzyme.

15. The process of claim 1 wherein acetolactate synthase enzyme is present as immobilized enzyme.

16. The process of claim 12 wherein the microorganism comprises a plasmid that comprises a DNA coding sequence that encodes for transaminase enzyme.

17. The process of claim 1 wherein acetolactate synthase enzyme is produced by a non-naturally occurring microorganism comprising a DNA coding sequence that encodes for acetolactate synthase enzyme.

18. The process of claim 17 wherein the microorganism comprises a plasmid that comprises a DNA coding sequence that encodes for acetolactate synthase enzyme.

19. The process of claim 16 wherein the plasmid is pME64.

20. The process of claim 18 wherein the plasmid is pPOT300 (ATCC Deposit PTA-1694).

21. The process of claim 9 wherein the whole cells are present in aqueous solution at a cell concentration of about 50 mg/ml to about 200 mg/ml.

22. The process of claim 21 wherein the whole cells are present in aqueous solution at a cell concentration of about 100 mg/ml.

23. The process of claim 13 wherein the whole cells are present in aqueous solution at a cell concentration of about 50 mg/ml to about 200 mg/ml.

24. The process of claim 23 wherein the whole cells are present in aqueous solution at a cell concentration of about 100 mg/ml.

25. A process for making an amino acid comprising:
   a) reacting a first amino acid with an enzyme under conditions appropriate to produce a keto acid;
   b) reacting the keto acid from (a) with a second amino acid and a transaminase enzyme under conditions appropriate to produce a third amino acid and pyruvate; and
   c) reacting pyruvate with acetolactate synthase enzyme under conditions appropriate to produce a compound that does not react with transaminase.

26. The process of claim 25 further comprising the step of isolating the third amino acid.

27. The process of claim 25 wherein the compound that does not react with transaminase enzyme is acetolactate.

28. The process of claim 25 wherein the compound that does not react with transaminase enzyme is acetoin.

29. The process of claim 25 wherein the first amino acid is L-threonine.

30. The process of claim 25 wherein the second amino acid is alanine.

31. The process of claim 25 wherein the second amino acid is L-aspartate.

32. The process of claim 25 wherein the keto acid is 2-ketobutyrate.

33. The process of claim 25 wherein in step (a) the enzyme is deaminase enzyme.

34. The process of claim 33 wherein deaminase enzyme is present in aqueous solution as whole cells producing deaminase enzyme.

35. The process of claim 33 wherein deaminase enzyme is present in aqueous solution as cell extracts of whole cells producing deaminase enzyme.

36. The process of claim 33 wherein deaminase enzyme is present as immobilized enzyme.

37. The process of claim 33 wherein deaminase enzyme is produced by a non-naturally occurring microorganism comprising a DNA coding sequence that encodes for deaminase enzyme.

38. The process of claim 37 wherein the microorganisms comprises a plasmid that comprises a DNA coding sequence that encodes for deaminase enzyme.

39. The process of claim 38 wherein the cell comprises a plasmid that comprises a DNA coding sequence that encodes for threonine deaminase enzyme.

40. The process of claim 39 wherein the plasmid is pME64.

41. The process of claim 25 wherein transaminase enzyme is present in aqueous solution as whole cells producing transaminase enzyme.

42. The process of claim 25 wherein transaminase enzyme is present in aqueous solution as cell extracts of whole cells producing transaminase enzyme.

43. The process of claim 25 wherein transaminase enzyme is present as immobilized enzyme.

44. The process of claim 25 wherein transaminase enzyme is produced by a non-naturally occurring microorganism comprising a DNA coding sequence that encodes for transaminase enzyme.

45. The process of claim 44 wherein the microorganism comprises a plasmid that comprises a DNA coding sequence that encodes for transaminase enzyme.

46. The process of claim 45 wherein the plasmid is pME64.

47. The process of claim 25 wherein acetolactate synthase enzyme is present in aqueous solution as whole cells producing acetolactate synthase enzyme.

48. The process of claim 25 wherein acetolactate synthase enzyme is present in aqueous solution as cell extracts of whole cells producing acetolactate synthase enzyme.

49. The process of claim 25 wherein acetolactate synthase enzyme is present as immobilized enzyme.

50. The process of claim 25 wherein acetolactate synthase enzyme is produced by a non-naturally occurring microorganism comprising a DNA coding sequence that encodes for acetolactate synthase enzyme.

51. The process of claim 50 wherein the microorganism comprises a plasmid that comprises a DNA coding sequence that encodes for acetolactate synthase enzyme.

52. The process of claim 51 wherein the plasmid is pPOT300 (ATCC Deposit PTA-1694).

53. The process of claim 34 wherein the whole cells are present in aqueous solution at a cell concentration of about 50 mg/ml to about 200 mg/ml.

54. The process of claim 53 wherein the whole cells are present in aqueous solution at a cell concentration of about 100 mg/ml.

55. The process of claim 41 wherein the whole cells are present in aqueous solution at a cell concentration of about 50 mg/ml to about 200 mg/ml.

56. The process of claim 55 wherein the whole cells are present in aqueous solution at a cell concentration of about 100 mg/ml.

57. The process of claim 47 wherein the whole cells are present in aqueous solution at a cell concentration of about 50 mg/ml to about 200 mg/ml.

58. The process of claim 57 wherein the whole cells are present in aqueous solution at a cell concentration of about 100 mg/ml.

59. A process for making L-2-aminobutyrate comprising:
   a) reacting L-threonine with threonine deaminase under conditions appropriate to produce 2-ketobutyrate;
   b) reacting the 2-ketobutyrate, L-aspartate and transaminase enzyme under conditions appropriate to produce oxaloacetate and L-2-aminobutyrate;
   c) allowing the oxaloacetate to form pyruvate;
   d) reacting the pyruvate with acetolactate synthase enzyme under conditions appropriate to produce acetolactate;
   e) allowing the acetolactate to form acetoin; and
   f) separately recovering acetoin and L-2-aminobutyrate.

60. Non-naturally occurring reaction medium consisting essentially of a keto acid, an amino acid, transaminase enzyme, and acetolactate synthase enzyme.

61. The reaction medium of claim 60 wherein the amino acid is alanine.

62. The reaction medium of claim 60 wherein the amino acid is L-aspartate.

63. The reaction medium of claim 60 wherein the keto acid is 2-ketobutyrate.

64. The reaction medium of claim 60 wherein transaminase enzyme is present in aqueous solution as whole cells producing transaminase enzyme.

65. The reaction medium of claim 60 wherein transaminase enzyme is present in aqueous solution as cell extracts of whole cells producing transaminase enzyme.

66. The reaction medium of claim 60 wherein transaminase enzyme is present as immobilized enzyme.

67. The reaction medium of claim 60 wherein acetolactate synthase enzyme is present in aqueous solution as whole cells producing acetolactate synthase enzyme.

68. The reaction medium of claim 60 wherein acetolactate synthase enzyme is present in aqueous solution as cell extracts of whole cells producing acetolactate synthase enzyme.

69. The reaction of claim 60 wherein acetolactate synthase enzyme is present as immobilized enzyme.

70. The reaction medium of claim 60 wherein acetolactate synthase enzyme is produced by a non-naturally occurring microorganism comprising a DNA coding sequence that encodes for acetolactate synthase enzyme.

71. The reaction medium of claim 70 wherein the microorganism comprises a plasmid that comprises a DNA coding sequence that encodes for acetolactate synthase enzyme.

72. The reaction medium of claim 70 wherein the plasmid is pPOT300 (ATCC Deposit PTA-1694).

73. The reaction medium of claim 60 further comprising a deaminase.

74. The reaction medium of claim 73 further comprising L-threonine.

75. Plasmid pPOT300 (ATCC Deposit PTA-1694).

76. The reaction medium of claim 65 wherein the whole cells are present in aqueous solution at a cell concentration of about 50 mg/ml to about 200 mg/ml.

77. The reaction medium of claim 76 wherein the whole cells are present in aqueous solution at a cell concentration of about 100 mg/ml.

78. The reaction medium of claim 60 wherein the whole cells are present in aqueous solution at a cell concentration of about 50 mg/ml to about 200 mg/ml.

79. The reaction medium of claim 78 wherein the whole cells are present in aqueous solution at a cell concentration of about 100 mg/ml.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 95 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO:1:

AAGCTTTTTT GTTGACAGCG TGAAAACAGT ACGGGTATAA TACTAAAGTC ACAAGGAGGA      60

TCCACTATGA CATCGGAAAA CCCGTTACTG GCGCT      95

(2) INFORMATION FOR SEQ ID NO:2:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic oligonucleotide"

(xi) SEQUENCE DESCRIPTION: SEQ ID NO:2:

CGCGGATCCA CTATGACCAC GAAGAAAGCT GATTACATTT GG      42

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:3:

CAGCGTGCAT GCTTATTGAT TAACTTGATC TAACCAGC                                38

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:4:

CCGGAATTCA CGTTGTGTCT CAAAATCTCT GAT                                     33

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:5:

CCGCTGCAGG CCGTCCCGTC AAGTCAGCGT AATG                                    34

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:6:

TTTGGATCCT CCTTAGTACA TGCAACC                                            27

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:7:

TTTGAATTCG GATGAAGATT CTTGCTCGAT TGT                                     33

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:8:

```
GGCGGCCGAC GCGCTGGGCT ACG                                          23
```

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:9:

```
CCCTCGCAAG CTCGTCCGGA GGCAAATCGC TGAATATTCC                        40
```

(2) INFORMATION FOR SEQ ID NO:10:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:10:

```
GATCCTAGGT ACCGGTGCGG CCGCATGCTG ACTGACTGAA GATCCCGGGC GATTCTACGC   60

CCGGGTTTTT TATG                                                    74
```

(2) INFORMATION FOR SEQ ID NO:11:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:11:

```
TCGACATAAA AAACCCGGGC GTAGAATCGC CCGGGATCTT CAGTCAGTCA GCATGCGGCC   60

GCACCGGTAC CTAG                                                    74
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:12:

GACCTCGAGG CACTTTGCGC CGAATAAATA CCTGTG            36

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:13:

GACCTGCAGC ACCAGGCGTT TAAGGGCACC AATAAC            36

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:14:

CGCGGATCCA TCATGGCTGA CTCGCAACCC C            31

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:15:

CTCGCATGCC AGGCATTTTT CCCTAACCCG CC            32

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:16:

TTTGAATCCA TCACAAGATA TTTAAAATTT            30

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:17:

TTTAGCGTCG ACGCATGCTC CTTTTATTTA GTGCTGTTC         39

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:18:

CGCGGATCCA CTATGTTTGA GAACATTACC GCC         33

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:19:

CAGCGTGCAT GCTTACAGCA CTGCCACAAT CGC         33

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:20:

GACGGATTCC CAGAGCAATC TCACGTCTTG C         31

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:21:

GACAGATCTC CCTGATAAGC GTAGCGCATC AGG         33

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "synthetic oligonucleotide"

(xi) SEQUENCE DESCRIPTION: SEQ ID NO:22:

GACGAATTCA CTTTACCGGT TGAATTTGC                                                29

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:23:

GACGGATCCT CCTTAGCCAA TATGTATTGC                                                30

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:24:

CTTGCATGCA CCATTCCTTG CGGCGGC                                                  27

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:25:

AGATCCGGAG GCAAATCGCT GAATATTCC                                                29

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:26:

CGCGGATCCA CTATGACCAC GAAGAAAGCT GATTACATTT GG                                 42

(2) INFORMATION FOR SEQ ID NO:27:

(i) SEQUENCE CHARACTERISTICS:
        (A) LENGTH: 38 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "synthetic oligonucleotide"

(xi) SEQUENCE DESCRIPTION: SEQ ID NO:27:

CAGCGTGCAT GCTTATTGAT TAACTTGATC TAACCAGC                    38